United States Patent
Kim et al.

(10) Patent No.: US 10,421,907 B2
(45) Date of Patent: *Sep. 24, 2019

(54) LIQUID CRYSTAL COMPOSITION AND A LIQUID CRYSTAL DISPLAY INCLUDING THE SAME

(71) Applicant: SAMSUNG DISPLAY CO., LTD., Yongin-si, Gyeonggi-Do (KR)

(72) Inventors: Min Hee Kim, Yongin-si (KR); So Youn Park, Yongin-si (KR); Tae Ho Kim, Yongin-si (KR); Mi Hwa Lee, Yongin-si (KR); Kyung Ho Park, Yongin-si (KR); Chang Hun Lee, Yongin-si (KR)

(73) Assignee: SAMSUNG DISPLAY CO., LTD., Yongin-si, Gyeonggi-Do (KR)

( * ) Notice: Subject to any disclaimer, the term of this patent is extended or adjusted under 35 U.S.C. 154(b) by 91 days.

This patent is subject to a terminal disclaimer.

(21) Appl. No.: 15/610,789

(22) Filed: Jun. 1, 2017

(65) Prior Publication Data

US 2018/0057741 A1    Mar. 1, 2018

(30) Foreign Application Priority Data

Aug. 25, 2016 (KR) .................. 10-2016-0108439

(51) Int. Cl.
*C09K 19/30* (2006.01)
*C07C 23/18* (2006.01)
(Continued)

(52) U.S. Cl.
CPC .......... *C09K 19/3098* (2013.01); *C07C 23/18* (2013.01); *C07C 25/18* (2013.01);
(Continued)

(58) Field of Classification Search
None
See application file for complete search history.

(56) References Cited

U.S. PATENT DOCUMENTS 7,495,715 B2   2/2009   Um et al.
7,767,280 B2   8/2010   Klasen-Memmer et al.
(Continued)

FOREIGN PATENT DOCUMENTS

CN    103254912    8/2013
CN    104593004    5/2015
(Continued)

OTHER PUBLICATIONS

Shin-Tson Wu et al., "Optimal operation temperature of liquid crystal modulators", Appl. Opt., vol. 26 No. 16, pp. 3441-3445, 1987.
(Continued)

*Primary Examiner* — Cynthia H Kelly
*Assistant Examiner* — Anna Malloy
(74) *Attorney, Agent, or Firm* — F. Chau & Associates, LLC

(57) ABSTRACT

A liquid crystal display includes a first base substrate, a second base substrate, an electrode part, and a liquid crystal layer. The second base substrate is disposed opposite to the first base substrate. The electrode part is disposed on at least one of the first base substrate and the second base substrate. The liquid crystal layer is disposed between the first base substrate and the second base substrate. The liquid crystal layer includes a liquid crystal composition. The liquid crystal composition includes at least one kind of liquid crystal compounds including a cyclopentadienyl group.

17 Claims, 5 Drawing Sheets

(51) Int. Cl.
*C09K 19/02* (2006.01)
*C09K 19/56* (2006.01)
*G02F 1/1333* (2006.01)
*G02F 1/1343* (2006.01)
*C07C 43/225* (2006.01)
*C07C 25/18* (2006.01)
*C09K 19/04* (2006.01)
*G02F 1/1337* (2006.01)
*C09K 19/12* (2006.01)

(52) U.S. Cl.
CPC ........ *C07C 43/225* (2013.01); *C09K 19/0208* (2013.01); *C09K 19/04* (2013.01); *C09K 19/3003* (2013.01); *C09K 19/3066* (2013.01); *C09K 19/56* (2013.01); *G02F 1/133365* (2013.01); *G02F 1/134363* (2013.01); *C07C 2601/10* (2017.05); *C07C 2601/14* (2017.05); *C09K 2019/0466* (2013.01); *C09K 2019/123* (2013.01); *C09K 2019/301* (2013.01); *C09K 2019/3004* (2013.01); *C09K 2019/3016* (2013.01); *C09K 2019/3019* (2013.01); *G02F 1/133711* (2013.01)

(56) References Cited

U.S. PATENT DOCUMENTS

| 7,785,675 | B2 | 8/2010 | Irisawa |
| 9,303,208 | B2 | 4/2016 | Yuan et al. |
| 9,404,037 | B2 | 8/2016 | Takeuchi et al. |
| 2005/0224756 | A1 | 10/2005 | Reiffenrath et al. |
| 2016/0054602 | A1 | 2/2016 | Tong et al. |
| 2016/0326434 | A1* | 11/2016 | Ahn ................ G02F 1/1368 |
| 2018/0046032 | A1* | 2/2018 | Kwon ............. C09K 19/3003 |

FOREIGN PATENT DOCUMENTS

| JP | 5769894 | 8/2015 |
| KR | 1020080075789 | 8/2008 |
| KR | 101374694 | 3/2014 |
| KR | 10-2016-0024774 | 3/2016 |
| WO | 2004000771 | 12/2003 |

OTHER PUBLICATIONS

Office Action issued in U.S. Appl. No. 15/487,514 dated Jun. 26, 2018.

Office Action issued in U.S. Appl. No. 15/487,514 dated Jan. 2, 2019.

* cited by examiner

LIQUID CRYSTAL COMPOSITION AND A LIQUID CRYSTAL DISPLAY INCLUDING THE SAME

CROSS-REFERENCE TO RELATED APPLICATION

The present application claims priority under 35 U.S.C. § 119 to Korean Patent Application No. 10-2016-0108439, filed on Aug. 25, 2016 in the Korean Intellectual Property Office, the disclosure of which is incorporated by reference herein in its entirety.

TECHNICAL FIELD

Exemplary embodiments of the present invention relate to a liquid crystal composition, and more particularly to a liquid crystal display including the same.

DISCUSSION OF RELATED ART

A liquid crystal display may include a first substrate, a second substrate, and a liquid crystal layer. The first substrate may include a plurality of pixel electrodes. The second substrate may include a common electrode. The liquid crystal layer may be disposed between the first substrate and the second substrate. The liquid crystal display may display an image by changing a light transmittance of the liquid crystal layer depending on electric fields formed between the respective pixel electrodes and the common electrode. The liquid crystal display may include a plurality of pixels. Each of the plurality of pixels may include the pixel electrode.

As liquid crystal displays implement two-dimensional images and three-dimensional images, a structure configured to provide a larger amount of image information to users may be needed. Accordingly, a liquid crystal display may be used. A liquid crystal display may have a relatively high reliability and a relatively fast driving speed.

SUMMARY

Exemplary embodiments of the present invention provide a liquid crystal composition and a liquid crystal display including the same. The liquid crystal composition may have a relatively low rotational viscosity.

Exemplary embodiments of the present invention provide a liquid crystal display. The liquid crystal display includes a first base substrate, a second base substrate, an electrode part, and a liquid crystal layer. The second base substrate is disposed opposite to the first base substrate. The electrode part is disposed on at least one of the first base substrate and the second base substrate. The liquid crystal layer is disposed between the first base substrate and the second base substrate. The liquid crystal layer includes a liquid crystal composition. The liquid crystal composition includes at least one liquid crystal compound represented by Formulae 1 to 3:

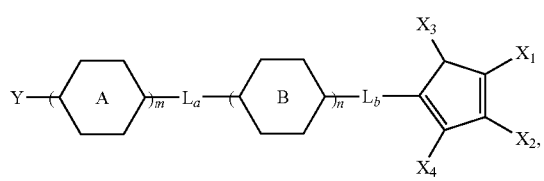

Formula 1

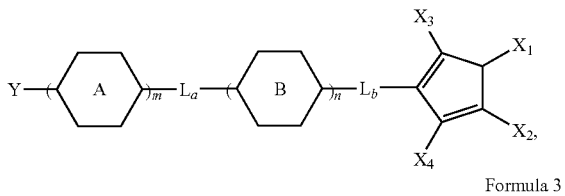

Formula 2

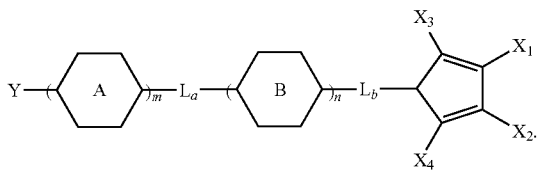

Formula 3

Y is selected from —H or an alkyl group of 1 to 10 carbon atoms, in which one or more —$CH_2$— groups are each independently unsubstituted or substituted by —C≡C—, —CH=CH—, —$CF_2$O—, —O—, —CO—O—, —O—CO—, or —O—CO—O— such that O atoms are not linked directly to each other, and a hydrogen atom is unsubstituted or substituted by a halogen atom.

A and B are each independently selected from 1,4-cyclohexylene or 1,4-phenylene, and —H of A and B are each independently unsubstituted or substituted by —F, —Cl, —$OCF_3$, —$CF_3$, —$CHF_2$, —$CH_2F$, or an alkyl or an alkoxy group of 1 or 2 carbon atoms.

n and m are each independently an integer selected from 0 to 2.

$X_1$ to $X_4$ are each independently selected from —H, —F, or —Cl, or an alkyl group of 1 or 2 carbon atoms.

$L_a$ and $L_b$ are each independently selected from a single bond, —C≡C—, —COO—, —OCO—, —$CF_2$O—, —$OCF_2$—, —$CH_2$O—, —CO—, —O—, —$(CH_2)_2$—, or —CH=CH—.

The liquid crystal compounds of Formulae 1 to 3 may be in an amount of more than 0% by weight to less than or equal to about 40% by weight with respect to the total liquid crystal composition.

The liquid crystal compound of Formula 1 may include at least one liquid crystal compound represented by Formula 1-1:

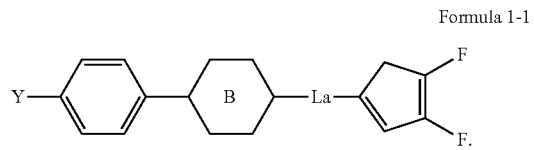

Formula 1-1

B, $L_a$, and Y are the same as defined in Formula 1.

The liquid crystal compound of Formula 1-1 may include at least one liquid crystal compound represented by the Chemical Formulae 1-1-1 and 1-1-2:

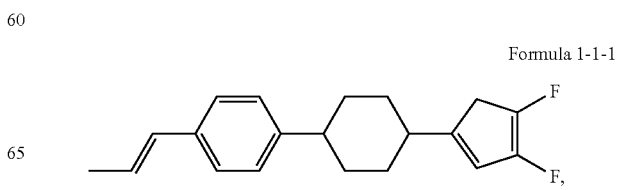

Formula 1-1-1

Formula 1-1-2

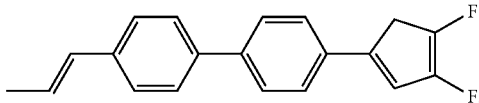

The liquid crystal composition may include at least one liquid crystal compound represented by Formula 4:

Formula 4

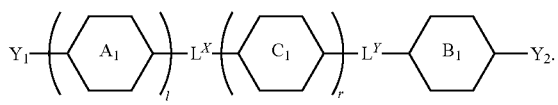

$Y_1$ and $Y_2$ may each independently be selected from —F, —Cl, or an alkyl group of 1 to 15 carbon atoms, in which one or more —$CH_2$— groups may be each independently be unsubstituted or substituted by —C≡C—, —CH=CH—, —$CF_2$O—, —O—, —CO—O—, —O—CO—, or —O—CO—O— such that O atoms are not linked directly to each other, and a hydrogen atom may be unsubstituted or substituted by a halogen atom.

$A_1$, $B_1$, and $C_1$ may each independently be selected from 1,4-cyclohexylene or 1,4-phenylene, and —H of $A_1$, $B_1$, and $C_1$ may each independently be unsubstituted or substituted by —F, —Cl, —$OCF_3$, —$CF_3$, —$CHF_2$, —$CH_2F$, or an alkyl or an alkoxy group of 1 or 2 carbon atoms.

l and r may each independently be an integer selected from 0 to 2.

$L^X$ and $L^Y$ may each independently be selected from a single bond, —C≡C—, —COO—, —OCO—, —$CF_2$O—, —$OCF_2$—, —$CH_2$O—, —CO—, —O—, —$(CH_2)_2$—, or —CH=CH—.

The liquid crystal composition may have a positive dielectric anisotropy.

The liquid crystal layer may be driven in a twisted nematic (TN) mode, an in-plane switching (IPS) mode, a plane-to-line switching (PLS) mode, or a fringe field switching (FFS) mode.

BRIEF DESCRIPTION OF THE DRAWINGS

The above and other features of the present invention will become more apparent by describing in detail exemplary embodiments thereof, with reference to the accompanying drawings, in which.

DETAILED DESCRIPTION OF THE EMBODIMENTS

Figure 1:
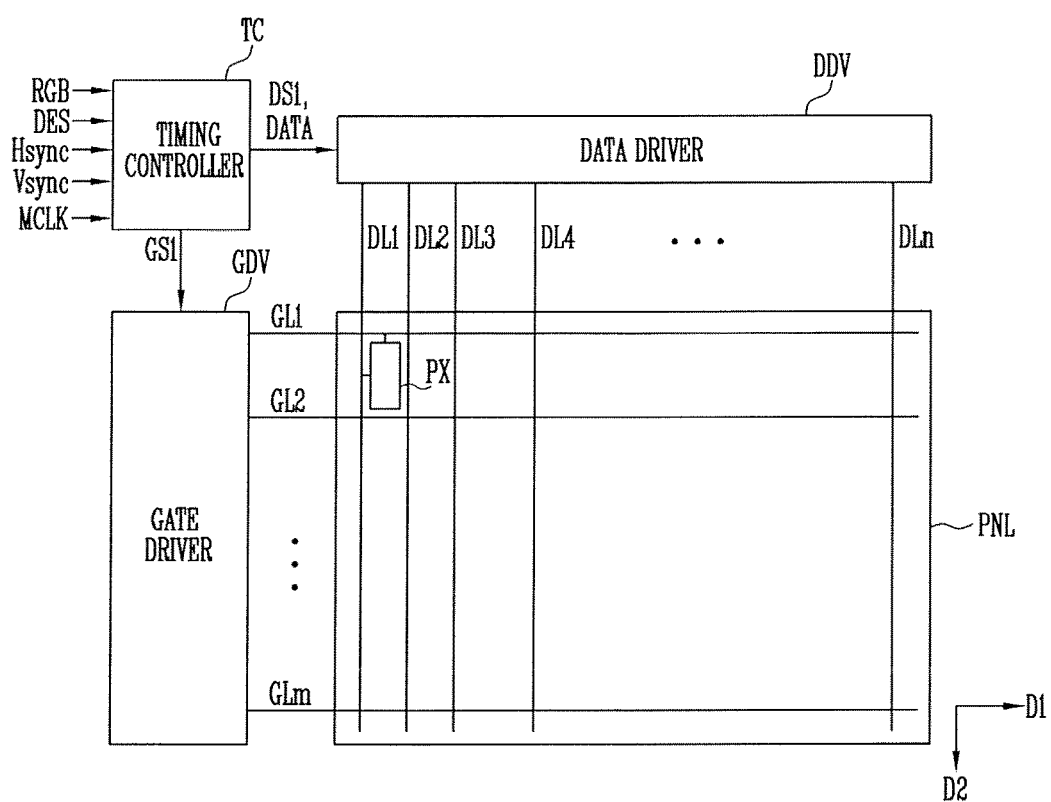
FIG. 1 is a schematic block diagram illustrating a liquid crystal display according to an exemplary embodiment of the present invention.

Exemplary embodiments of the present invention will be described below in more detail with reference to the accompanying drawings. In this regard, the exemplary embodiments may have different forms and should not be construed as being limited to the exemplary embodiments of the present invention described herein.

Like reference numerals may refer to like elements throughout the specification and drawings.

It will be understood that although the terms "first" and "second" may be used herein to describe various components, these components should not be limited by these terms.

Sizes of elements in the drawings may be exaggerated for clarity of description.

It will be understood that when a component, such as a layer, a film, a region, or a plate, is referred to as being "on" another component, the component can be directly on the other component or intervening components may be present.

Exemplary embodiments of the present invention relate to a liquid crystal composition and a liquid crystal display including the same. The liquid crystal composition may have a negative dielectric anisotropy.

A liquid crystal composition according to an exemplary embodiment of the present invention may include at least one liquid crystal compound having a cyclopentadienyl group. A liquid crystal compound having a cyclopentadienyl group according to an exemplary embodiment of the present invention may be represented by the following Formulae 1 to 3.

Formula 1

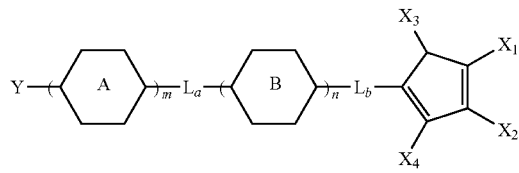

Formula 2

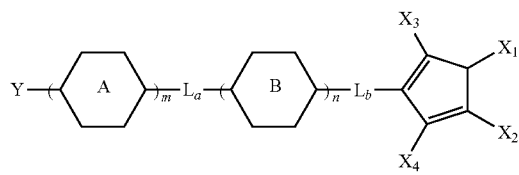

Formula 3

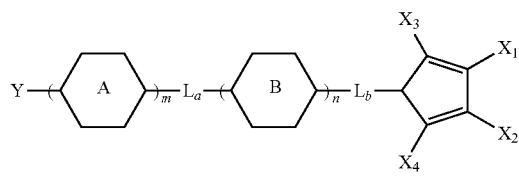

In Formulae 1 to 3, Y may be selected from —H or an alkyl group of 1 to 10 carbon atoms. One or more —$CH_2$— groups of the alkyl group may be each independently be unsubstituted or substituted by —C≡C—, —CH=CH—, —$CF_2$O—, —O—, —CO—O—, —O—CO—, or —O—CO—O—. Thus, O atoms might not be linked directly to each other and hydrogen atom may be unsubstituted or substituted by halogen atom.

In Formulae 1 to 3, A and B may each independently be selected form 1,4-cyclohexylene or 1,4-phenylene. —H of A and B may be each be independently unsubstituted or substituted by —F, —Cl, —OCF$_3$, —CF$_3$, —CHF$_2$, —CH$_2$F, or an alkyl or an alkoxy group of 1 or 2 carbon atoms.

In Formulae 1 to 3, n and m may each independently be an integer selected from 0 to 2;

$X_1$ to $X_4$ may each independently be selected from —H, —F, or —Cl, or an alkyl group of 1 or 2 carbon atoms; and $L_a$ and $L_b$ may each independently be selected from a single bond, —C≡C—, —COO—, —OCO—, —CF$_2$O—, —OCF$_2$—, —CH$_2$O—, —CO—, —O—, —(CH$_2$)$_2$—, or —CH=CH—.

According to an exemplary embodiment of the present invention, the liquid crystal compound having the cyclopentadienyl group may be in an amount of more than 0% by weight to less than or equal to about 40% by weight with respect to the total liquid crystal composition. Thus, the liquid crystal compounds of Formulae 1 to 3 may each be in an amount of more than 0% by weight to less than or equal to about 40% by weight with respect to the total liquid crystal composition. For example, according to an exemplary embodiment of the present invention, the liquid crystal composition may include the liquid crystal compound represented by Formula 1, Formula 2, or Formula 3 in an amount of more than 0% by weight to less than or equal to about 40% by weight with respect to the total liquid crystal composition. Alternatively, the liquid crystal composition may include the liquid crystal compounds represented by Formulae 1 and 2 in an amount of more than 0% by weight less than or equal to about 40% by weight with respect to the total liquid crystal composition. The liquid crystal composition may include the liquid crystal compounds represented by Formulae 1 to 3 in an amount of more than 0% by weight to less than or equal to about 40% by weight with respect to the total liquid crystal composition.

When the liquid crystal composition omits the liquid crystal compounds of Formulae 1 to 3, the liquid crystal compound might not have certain characteristics described in more detail below, which may be present by the inclusion of liquid crystal compounds of Formulae 1 to 3. When the amount of the liquid crystal compounds of Formulae 1 to 3 exceeds about 40% by weight with respect to the liquid crystal composition, it may be relatively difficult to control the dielectric anisotropy, refractive anisotropy, rotational viscosity of the total liquid crystal composition.

The liquid crystal compounds of Formulae 1 to 3 may have a substituted or unsubstituted cyclopentadienyl group. Thus, a relatively low rotational viscosity may be maintained. A double bond in the cyclopentadienyl group may be unsubstituted or substituted by a halogen group or an alkyl group. Thus, as the halogen group or the alkyl group are included in the liquid crystal compound, a steric hindrance effect may occur. Accordingly, a reaction of the double bond with another functional group having a relatively high reactivity may be reduced or eliminated.

In the liquid crystal composition according to an exemplary embodiment of the present invention, a decrease in the rotational viscosity of the liquid crystal compound may increase the response speed of the liquid crystal display, for example, when the liquid crystal compound is included in the liquid crystal display. When the time for changing the liquid crystal molecules by an electric field is a rising time, and the time for returning the changed liquid crystal molecules to their original state is a falling time Toff, the falling time and the rotational viscosity may satisfy the following equation. In the equation, $\gamma_1$ may refer to a rotational viscosity of the liquid crystal molecules; d may refer to a distance between a first substrate and a second substrate, for example, a cell gap; and $K_{33}$ may refer to a bending elastic modulus.

$$Toff \propto \frac{\gamma_1 d^2}{K_{33}} \quad \text{[Equation]}$$

According to an exemplary embodiment of the present invention, the rotational viscosity of the liquid crystal compound may decrease, and accordingly, the falling time may decrease. Thus, the response speed of the liquid crystal display may increase.

According to an exemplary embodiment of the present invention, the liquid crystal compound of Formula 1 may include at least one of liquid crystal compounds represented by the following Formula 1-1. According to an exemplary embodiment of the present invention, the liquid crystal compounds of Formulae 2 and 3 may include various types of liquid crystal compounds.

According to an exemplary embodiment of the present invention, the liquid crystal compound of Formula 1 may include at least one of the liquid crystal compounds represented by the following Formula 1-1.

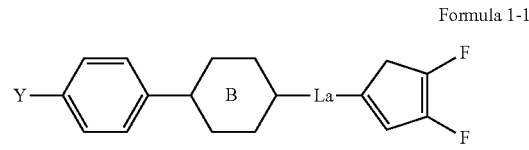

Formula 1-1

In Formula 1-1, B, $L_a$, and Y may be the same as defined with reference to Formula 1.

According to an exemplary embodiment of the present invention, the liquid crystal compound of Formula 1-1 may include at least one of liquid crystal compounds represented by the following Formulae 1-1-1 and 1-1-2.

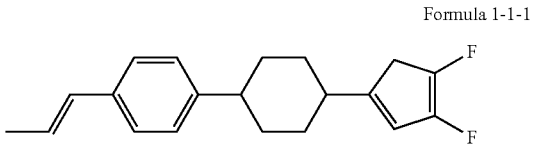

Formula 1-1-1

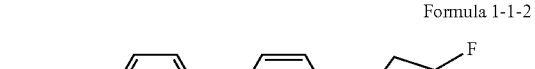

Formula 1-1-2

The liquid crystal compounds represented by Formulae 1-1-1 and 1-1-2 may include a cyclopentadienyl group. Thus, a relatively low rotational viscosity and a relatively high refractive anisotropy may be maintained. The relatively low rotational viscosity may be from the double bond of the cyclopentadienyl group.

The liquid crystal composition according to an exemplary embodiment of the present invention may include at least one of liquid crystal compounds represented by the following Formula 4 together with the above-described liquid crystal compounds having a cyclopentadienyl group.

Formula 4

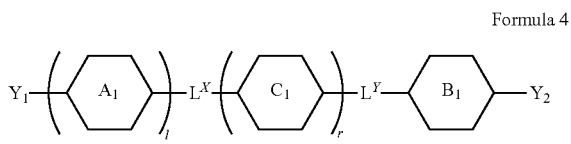

In Formula 4, $Y_1$ and $Y_2$ may each independently be selected from —F, —Cl, or an alkyl group of 1 to 15 carbon atoms. In the alkyl group, one or more —$CH_2$— groups may be each independently be unsubstituted or substituted by —C≡C—, —CH=CH—, —$CF_2$O—, —O—, —CO—O—, —O—CO—, or —O—CO—O—. Thus, O atoms might not be linked directly to each other. —H may be unsubstituted or substituted by halogen atom.

In Formula 4, $A_1$, $B_1$, and $C_1$ may each independently be selected from 1,4-cyclohexylene or 1,4-phenylene. —H of $A_1$, $B_1$, and $C_1$ may each independently be unsubstituted or substituted by —F, —Cl, —$OCF_3$, —$CF_3$, —$CHF_2$, —$CH_2F$, or an alkyl or an alkoxy group of 1 or 2 carbon atoms.

In Formula 4, l and r may each independently be an integer selected from 0 to 2.

In Formula 4, $L^X$ and $L^Y$ may each independently be selected from a single bond, —C≡C—, —COO—, —OCO—, —$CF_2$O—, —$OCF_2$—, —$CH_2$O—, —CO—, —O—, —$(CH_2)_2$—, or —CH=CH—.

The liquid crystal composition according to an exemplary embodiment of the present invention may have a positive dielectric anisotropy. In individual liquid crystal compounds, some of the liquid crystal compounds may have a negative dielectric anisotropy; however, the liquid crystal composition including the total sum of the liquid crystal compounds may have a positive dielectric anisotropy.

The liquid crystal composition according to an exemplary embodiment of the present invention may include a monomer. The monomer may be polymerized, for example, to form an alignment layer. The monomer may be represented by Formula 5.

Formula 5

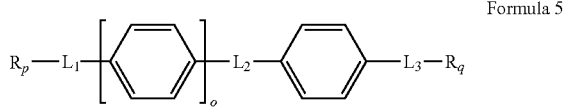

In Formula 5, $R_p$ and $R_q$ may each independently be a reactive group of 1 to 6 carbon atoms. The reactive group may produce a polymerization reaction. The reactive group may be selected from an acrylate group, a methacrylate group, an epoxy group, an oxetane group, a vinyl-ether group, or a styrene group of 1 to 12 carbon atoms.

In Formula 5, $L_1$ to $L_3$ may each independently be selected from a single bond, or an ether group, a carbonyl group, or a carboxyl group of 1 or 2 carbon atoms.

In Formula 5, o may be an integer selected from 1 or 2.

In addition to the liquid crystal compounds, the liquid crystal composition may include various additives.

The liquid crystal composition may include an antioxidant. The liquid crystal composition may include a stabilizer. Various substances may be the stabilizer. For example, the stabilizer may be a hindered amine light stabilizer (HALS)-based stabilizer.

The liquid crystal composition according to an exemplary embodiment of the present invention may be included in liquid crystal displays. The liquid crystal displays may have a twisted nematic (TN) mode, a super-twisted nematic (STN) mode, an optically compensated bend (OCB) mode, an in-plane switching (IPS) mode, or a fringe field switching (FFS) mode. Among these modes, the IPS, PLS, and FFS modes may be modes in which an electric field is horizontally applied to the liquid crystal display. The liquid crystal composition according to an exemplary embodiment of the present invention may be included in the above-described modes. Particularly, the liquid crystal composition according to an exemplary embodiment of the present invention may be included in the IPS mode. In the IPS mode, since a twist elastic constant that is smallest among elastic constants of liquid crystals may be used, the IPS mode has a relatively slower response time than the vertical field modes (e.g., the TN, STN, and OCB modes). The IPS mode requires, as a property of the liquid crystal composition, a low rotational viscosity as compared with the vertical field modes. Accordingly, the liquid crystal composition according to the embodiment of the present disclosure satisfies the low rotational viscosity. This will be described as follows with reference to the accompanying drawings.

FIG. 1 is a schematic block diagram illustrating a liquid crystal display according to an exemplary embodiment of the present invention.

Referring to FIG. 1, a liquid crystal display according to an exemplary embodiment of the present invention may include a display panel PNL, a timing controller TC, a gate driver GDV, and a data driver DDV.

The display panel PNL may be a liquid crystal panel. The display panel PNL may include a first substrate, a second substrate, and a liquid crystal layer. The liquid crystal layer may be disposed between the first substrate and the second substrate.

The display panel PNL may include a plurality of gate lines GL1 to GLm and a plurality of data lines DL1 to DLn. The gate lines GL1 to GLm may extend in a first direction D1 (e.g., a row direction). The data lines DL1 to DLn may extend in a second direction D2 (e.g., a column direction). The second direction D2 may intersect the first direction D1. The display panel PNL may include a plurality of pixels PX. The pixels PX may be arranged in the first direction D1. The pixels PX may be arranged in the second direction D2.

The timing controller TC may receive image data RGB and a control signal from an external graphic controller. The control signal may include a vertical synchronization signal Vsync, a horizontal synchronization signal Hsync, a data enable signal DES, and a main clock signal MCLK. The vertical synchronization signal Vsync may be a row distinction signal. The horizontal synchronization signal Hsync may be a row distinction signal. The data enable signal DES may have a relatively high level for a section of the timing controller TC in which data is output to display an area into which the data enters.

The timing controller TC may convert the image data RGB according to specifications of the data driver DDV. The timing controller may output the converted image data DATA to the data driver DDV. The timing controller TC may generate a gate control signal GS1 and a data control signal DS1. The data control signal DS1 may be based on the control signal from the external graphic controller. The timing controller TC may output the gate control signal GS1 to the gate driver GDV. The timing controller TC may output the data control signal DS1 to the data driver DDV. The gate control signal GS1 may be a signal for driving the date driver GDV. The data control signal DS1 may be a signal for driving the data driver DDV.

The gate driver GDV may generate a gate signal based on the gate control signal GS1. The gate driver GDV may output the gate signal to each of the gate lines GL1 to GLm. The gate control signal GS1 may include a scan start signal, at least one clock signal, or an output enable signal. The scan start signal may instruct a scan start. The at least one clock signal may control the output period of the gate-on voltage. The output enable signal may limit a maintenance time of a gate-on voltage.

The data driver DDV may generate a gray scale voltage. The gray scale voltage may correspond to the image data DATA. The gray scale voltage may be based on the data control signal DS1. The data driver DDV may output the gray scale voltage as a data voltage, for example, to each of the data lines DL1 to DLn. The data voltage may include a positive data voltage and a negative data voltage. The positive data voltage may have a positive value with respect to a common voltage. The negative data voltage may have a negative value with respect to the common voltage. The data control signal DS1 may include a horizontal start signal, a load signal, or an inversion signal. The horizontal start signal may inform a start of transmission of the image data DATA to the data driver DDV. The load signal may instruct to apply the data voltage to the data lines DL1 to DLn. The inversion signal may invert the polarity of the data voltage with respect to the common voltage.

Each of the timing controller TC, the gate driver GDV, and the data driver DDV may be directly disposed on the display panel PNL as at least one integrated circuit chip, a flexible printed circuit board to be attached to the display panel PNL in the form of a tape carrier package (TCP), or a separate printed circuit board. Alternatively, at least one of the gate driver GDV and the data driver DDV may be integrated on the display panel PNL together with the gate lines GL1 to GLm, the data lines DL1 to DLn, and transistors. The timing controller TC, the gate driver GDV, and the data driver DDV may be integrated as a single chip.

The liquid crystal display described with reference to FIG. 1 may be implemented in various forms.

Figure 2:
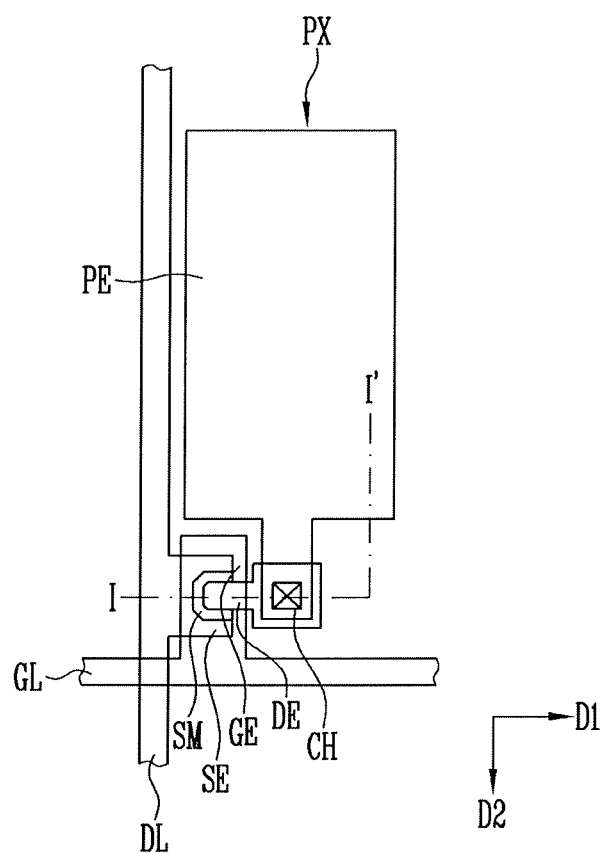
FIG. 2 is a plan view illustrating a liquid crystal display in a TN mode according to an exemplary embodiment of the present invention.
Figure 3:
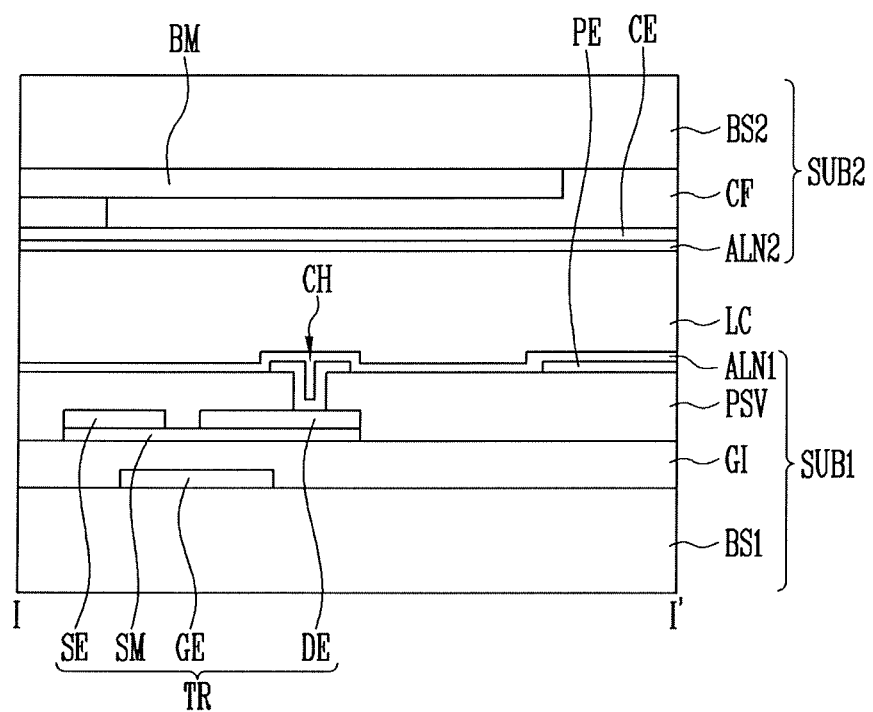
FIG. 3 is a cross-sectional view taken along a line I-I' of FIG. 2 according to an exemplary embodiment of the present invention.
Figure 4:
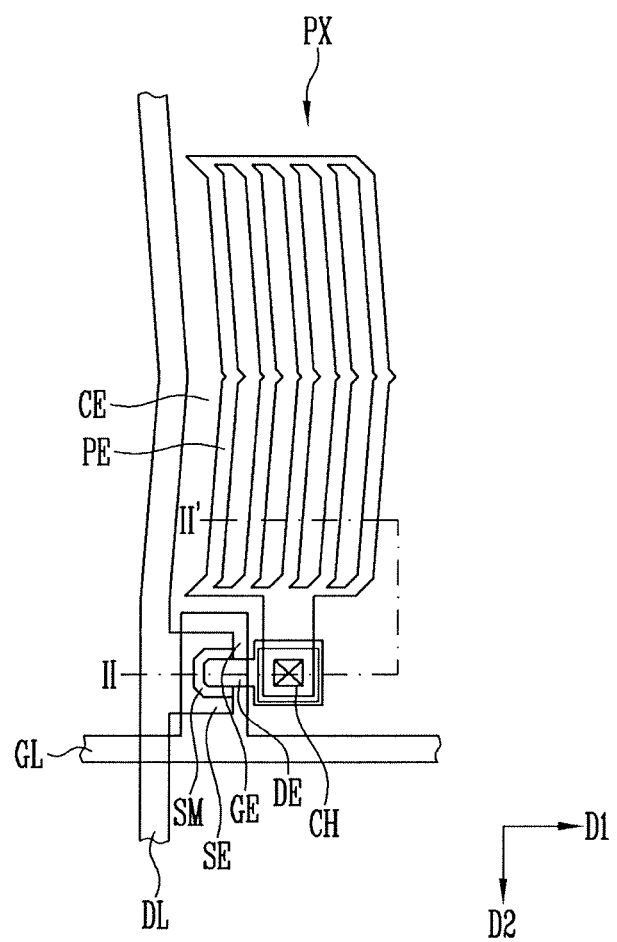
FIG. 4 is a plan view illustrating a liquid crystal display in a PLS mode according to an exemplary embodiment of the present invention.
Figure 5:
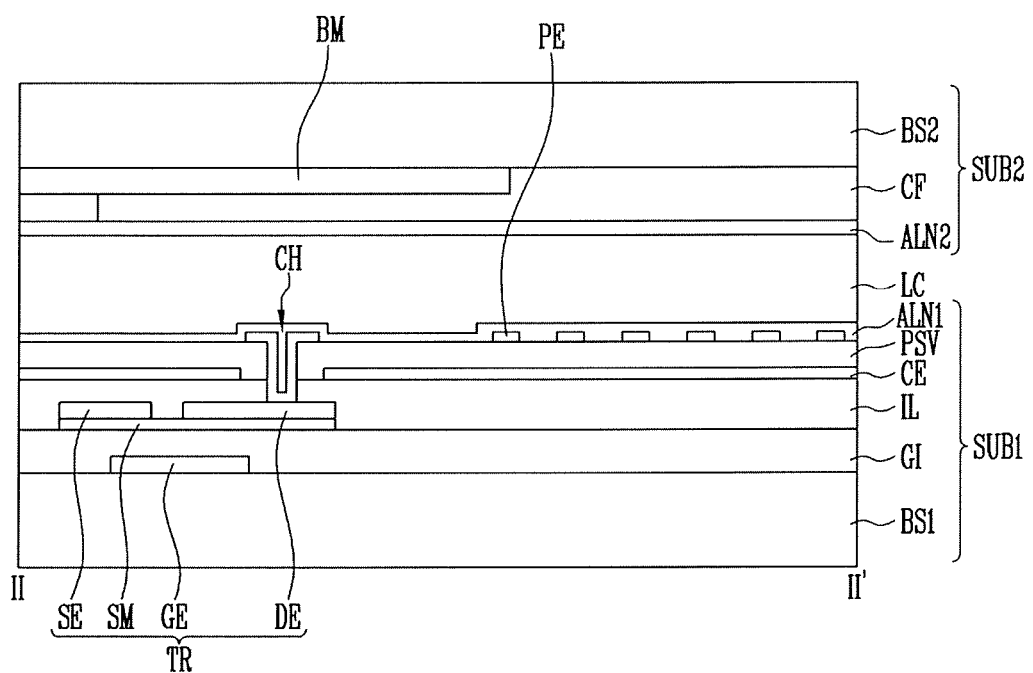
FIG. 5 is a cross-sectional view taken along a line II-II' of FIG. 4 according to an exemplary embodiment of the present invention.

FIG. 2 is a plan view illustrating a liquid crystal display in a TN mode according to an exemplary embodiment of the present invention. FIG. 3 is a cross-sectional view taken along a line I-I' of FIG. 2 according to an exemplary embodiment of the present invention. FIG. 4 is a plan view illustrating a liquid crystal display in a PSL mode according to an exemplary embodiment of the present invention. FIG. 5 is a cross-sectional view taken along a line II-II' of FIG. 4 according to an exemplary embodiment of the present invention.

Referring to FIGS. 2 and 3, the liquid crystal display according to an exemplary embodiment of the present invention may include a first substrate SUB1, a second substrate SUB2, and a liquid crystal layer LC. The second substrate SUB2 may be disposed opposite the first substrate SUB1. The liquid crystal layer LC may be disposed between the first substrate SUB1 and the second substrate SUB2.

The first substrate SUB1 may include a first base substrate BS1, a line unit, a plurality of pixels PX, and a first alignment layer ALN1. The line unit may be positioned over the first substrate SUB1. The pixels PX may be connected to the line unit. The first alignment layer ALN1 may be positioned over the pixels PX.

The pixel PX may be connected to a corresponding data line among sequentially arranged data lines and a corresponding gate line among adjacent gate lines. According to an exemplary embodiment of the present invention, a gate line to which the pixel PX may be connected may be referred to as a gate line GL. A data line to which the pixel PX may be connected may be referred to as a data line DL.

The pixel PX may be connected to a transistor TR. The transistor TR may be connected to each of the gate line GL and the data line DL.

The first base substrate BS1 may have a substantially quadrangular shape. The first base substrate BS1 may include a transparent insulating material.

The line unit may include gate lines GL and data lines DL.

The gate line GL may be disposed on the first base substrate BS1. The gate line GL may extend in a first direction D1.

A gate insulating layer GI may be disposed on the first base substrate BS1 on which the gate line GL may be disposed. The gate insulating layer GI may include an insulating material. For example, the gate insulating layer GI may include silicon nitride or silicon oxide.

The data line DL may extend in a second direction D2. The second direction D2 may intersect the first direction D1. The gate line GL and the gate insulating layer GI may extend in the first direction D1.

The transistor TR may be connected to each of the gate line GL and the data line DL. Referring to FIG. 1, in substantially all of the pixels PX, each of the gate line, the data line, and the transistor may be provided in plurality. Thus, each transistor may be connected to a corresponding one of the plurality of gate lines and a corresponding one of the plurality of data lines. The transistor TR may include a gate electrode GE, a semiconductor pattern SM, a source electrode SE, and a drain electrode DE.

The gate electrode GE may protrude from the gate line GL. Alternatively, the gate electrode GE may be disposed on a partial region of the gate line GL.

The gate electrode GE may include a metal. The gate electrode GE may include at least one of nickel, chrome, molybdenum, aluminum, titanium, copper, tungsten, or an alloy thereof. The gate electrode GE may have a single layered structure or multi-layered structure, which each may be formed, for example, by using the metal. For example, the gate electrode GE may have a tri-layered structure in which molybdenum, aluminum, and molybdenum are sequentially stacked. Alternatively, the gate electrode GE may have a double layered structure in which titanium and copper are sequentially stacked. The gate electrode GE may have a single layered structure including an alloy of titanium and copper.

The semiconductor pattern SM may be disposed on the gate insulating layer GI. The semiconductor pattern SM may be disposed on the gate electrode GE with the gate insulating layer GI interposed therebetween. A partial region of the semiconductor pattern SM may overlap with the gate electrode GE. The semiconductor pattern SM may be a doped or an undoped silicon thin film or a silicon thin film. The silicon thin film may be amorphous or crystalline. The semiconductor pattern SM may be a crystalline or amorphous oxide semiconductor thin film.

The source electrode SE may diverge from the data line DL. The source electrode SE may be disposed on the semiconductor pattern SM. A partial region of the source electrode SE may overlap with the gate electrode GE.

The drain electrode DE may be spaced apart from the source electrode SE. The semiconductor pattern SM may be disposed between the drain electrode DE and the source electrode SE. The drain electrode DE may be formed on the semiconductor pattern SM. A partial region of the drain electrode DE may overlap with the gate electrode GE.

The source electrode SE and the drain electrode DE may each include nickel, chrome, molybdenum, aluminum, titanium, copper, tungsten, an alloy thereof, or any combination thereof. The source electrode SE and the drain electrode DE may each have a single layered structure or multi-layered, for example, using the metal. For example, each of the source electrode SE and the drain electrode DE may have a double layered structure in which titanium and copper are sequentially stacked. Alternatively, each of the source electrode SE and the drain electrode DE may have a single layered structure including an alloy of titanium and copper.

The source electrode SE and the drain electrode DE may be spaced apart from each other. Thus, an upper surface of the semiconductor pattern SM may be exposed between the source electrode SE and the drain electrode DE. The semiconductor pattern SM disposed between the source electrode SE and the drain electrode DE may form a conductive channel between the source electrode SE and the drain electrode DE. A conductivity of the conductive channel may be based on whether a voltage is applied the gate electrode GE.

A protective layer PSV may be positioned over each of the source electrode SE and the drain electrode DE. The protective layer PSV may cover each of the source electrode SE, the drain electrode DE, a channel part, and the gate insulating layer GI. The protective layer PSV may substantially cover a contact hole CH. A portion of the drain electrode DE may be exposed through the contact hole CH. The protective layer PSV may include, for example, silicon nitride or silicon oxide. According to an exemplary embodiment of the present invention, the protective layer PSV may have a single layered structure; however, exemplary embodiments of the present invention are not limited thereto. An insulating layer such as the protective layer PSV may have a multi-layered structure.

The pixel electrode PE may be connected to the drain electrode DE, for example, through the contact hole CH of the protective layer PSV.

The pixel electrode PE may include a transparent conductive material. The pixel electrode PE may include a transparent conductive oxide. The transparent conductive oxide may be indium tin oxide (ITO), indium zinc oxide (IZO), or indium tin zinc oxide (ITZO).

The first alignment layer ALN1 may be positioned over the pixel electrode PE. The first alignment layer ALN1 may align liquid crystal molecules of the liquid crystal layer LC. The first alignment layer ALN1 may include a polymer. The polymer may be polymerized by the monomer represented by Formula 5 as described herein. The monomer of Formula 5 may have, as a terminal group, a reactive group of 1 to 6 carbon atoms. The monomer may produce a polymerization reaction. The polymerization reaction may be produced by the reactive group. The reactive group may be an acrylate group, a methacrylate group, an epoxy group, an oxetane group, a vinyl-ether group, or a styrene group of 1 to 12 carbon atoms. Another reactive group producing a polymerization reaction may be used.

The second substrate SUB2 may include a second base substrate BS2, color filters CF, a black matrix BM, a common electrode CE, and a second alignment layer ALN2.

The color filters CF may be disposed on the second base substrate BS2, for example, corresponding to the respective pixels PX. The color filters CF may represent the color red, the color green, and the color blue, respectively. However, exemplary embodiments of the present invention are not limited thereto. The color filters CF may represent various colors such as white, yellow, cyan, or magenta.

The black matrix BM may be disposed between the color filters CF. The black matrix BM may surround each of the color filters CF. The black matrix BM may block light transmitted through the liquid crystal layer LC between adjacent pixels.

According to an exemplary embodiment of the present invention, the color filter CF and the black matrix BM may be disposed in the second substrate SUB2; however, a position of the color filter CF and/or the black matrix BM is not limited thereto. For example, the color filter CF and the black matrix BM may each be provided in the first substrate SUB1.

The common electrode CE may be disposed on each of the color filter CF and the black matrix BM. The common electrode CE may form an electric field together with the pixel electrode PE. Thus, the liquid crystal layer LC may be driven. The common electrode CE may include a transparent conductive material. The common electrode CE may include a conductive metal oxide such as tin oxide (ITO), indium zinc oxide (IZO), or indium tin zinc oxide (ITZO).

The second alignment layer ALN2 may be disposed over the common electrode CE. The second alignment layer ALN2 may be disposed over the common electrode CE, for example, to align the liquid crystal molecules of the liquid crystal layer LC.

The second alignment layer ALN2 may include a polymer. The polymer may be polymerized by the monomer represented by Formula 5 described herein. The monomer of Formula 5 may have, as a terminal group, a reactive group of 1 to 6 carbon atoms. The monomer may produce a polymerization reaction. The polymerization reaction may be produced by the reactive group. The reactive group may be an acrylate group, a methacrylate group, an epoxy group, an oxetane group, a vinyl-ether group, or a styrene group of 1 to 12 carbon atoms. Another reactive group producing a polymerization reaction may be used.

The liquid crystal layer LC may be disposed between the first substrate SUB1 and the second substrate SUB2. The liquid crystal layer LC may include a liquid crystal compound. The liquid crystal layer LC may include the liquid crystal composition according to an exemplary embodiment of the present invention.

In the liquid crystal display, if a gate signal is applied to the gate line GL, the thin film transistor TR may be turned on. Thus, a data signal applied to the data line DL may applied to the pixel electrode PE through the thin film transistor TR. If the data signal is applied to the pixel electrode PE as the thin film transistor TR is turned on, an electric field may be formed between the pixel electrode PE and the common electrode CE. The liquid crystal molecules may be driven by the electric field generated by a difference in voltage between the common electrode CE and the pixel electrode PE. Accordingly, an amount of light transmitted through the liquid crystal layer LC may be changed. Thus, an image may be displayed.

A liquid crystal display according to an exemplary embodiment of the present invention will be described in more detail below with reference to FIGS. 4 and 5. Portions different from those described above will be mainly be described.

The liquid crystal display described with reference to FIGS. 4 and 5 may be substantially the same as the liquid crystal display described above with reference to FIGS. 1 to 3, and thus duplicative descriptions may be omitted below, and differences between the liquid crystal displays may be focused on below.

Referring to FIGS. 4 and 5, the liquid crystal display according to an exemplary embodiment of the present invention may include a first substrate SUB1, a second substrate SUB2, and a liquid crystal layer LC. The second substrate SUB2 may be disposed opposite the first substrate SUB1. The liquid crystal layer LC may be disposed between the first substrate SUB1 and the second substrate SUB2.

In the liquid crystal display according to an exemplary embodiment of the present invention, pixel electrodes PE and a common electrode CE may be provided on the same substrate, for example, the first substrate SUB1. Thus, the first substrate SUB1 may include a first base substrate BS1, a line unit, a plurality of pixels PX, the common electrode CE, and a first alignment layer ALN1. The line unit may be disposed on the first base substrate BS1. The pixels PX may be connected to the line unit. The common electrode may be disposed on the first base substrate BS1. The first alignment layer ALN1 may be disposed over the pixels PX.

The pixel PX may be connected to a transistor TR. The transistor TR may be connected to a gate line GL and a data line DL.

The transistor TR may include a gate electrode GE, a semiconductor pattern SM, a source electrode SE, and a drain electrode DE.

An interlayer layer IL may be positioned over each of the source electrode SE and the drain electrode DE. The interlayer layer IL may include an organic insulating material or an inorganic insulating material. For example, the interlayer layer IL may include silicon nitride or silicon oxide.

A protective layer PSV may be disposed on the interlayer layer IL. The protective layer PSV may include, for example, silicon nitride or silicon oxide.

A contact hole CH may be formed in each of the interlayer layer IL and the protective layer PSV. The contact hole CH may expose a portion of an upper surface of the drain electrode DE.

The pixel electrode PE may be formed on the protective layer PSV. The pixel electrode PE may be connected to the drain electrode DE, for example, through the contact hole CH. The pixel electrode PE may have a plurality of branches. The branches may be spaced apart from each other at a predetermined distance. The branches may form an electric field together with the common electrode CE. The shape of the branches is not limited thereto, and the branches may be provided in various shapes.

The common electrode CE may be disposed between the interlayer layer IL and the protective layer PSV. The common electrode CE may have the shape of a whole plate, for example, to cover all pixel regions. The shape of the common electrode CE is not limited thereto. The common electrode CE may have various shapes as long as the common electrodes are connected to each other in adjacent pixel regions such that substantially the same common voltage is applied thereto. The region in which the contact hole CH is provided may have an opening. The common electrode may be removed from the opening. The common electrode CE and the pixel electrode PE may be insulated from each other. For example, the protective layer PSV may be disposed between the common electrode CE and the pixel electrode PE. The common electrode CE, the pixel electrode PE, and the protective layer PSV may form a storage capacitor Cst of each pixel PX.

The pixel electrode PE and the common electrode CE may include a transparent conductive material.

The second substrate SUB2 may be disposed opposite to the first substrate SUB1. The second substrate SUB2 may include a second base substrate SB2, color filters CF, a black matrix BM, and a second alignment layer ALN2.

The liquid crystal layer LC may include a liquid crystal composition described herein according to an exemplary embodiment of the present invention.

The common electrode may have the shape of a whole plate, the pixel electrode may have branches, and the liquid crystal display may be driven in a plane-to-line switching (PLS) mode. However, exemplary embodiments of the present invention are not limited thereto. For example, the common electrode may have a plurality of branches. The branches of the pixel electrode may be alternately disposed with the branches of the common electrode on a plane such that the liquid crystal display is driven in the IPS mode. The structure of the liquid crystal display may have another mode other than the PLS mode or the IPS mode.

According to an exemplary embodiment of the present invention, two gate lines and one data line may be connected to one pixel. According to an exemplary embodiment of the present invention, one gate line and two data lines may be connected to one pixel. Alternatively, one pixel may have two sub-pixels to which two voltages different from each other are applied. Thus, a relatively high voltage may be applied to one sub-pixel, and a relatively low voltage may be applied to the other sub-pixel. Each of the components in the pixel, e.g., the gate electrode, the source electrode, the drain electrode, and the like may be disposed in a structure different from exemplary embodiments described herein.

EXAMPLES

1. Properties of Liquid Crystal Compounds

Exemplary property values of liquid crystal compounds of Comparative Example 1, Comparative Example 2, and Embodiment 1 are shown in Table 1.

TABLE 1

| Liquid Crystal Compound | Tni (° C.) | Δn | Δε | γ1 (mPa · s) |
|---|---|---|---|---|
| Comparative Example 1 | 74 | 0.075 | 9.7 | 160 |
| Comparative Example 2 | 99 | 0.07 | 9.8 | 184 |
| Embodiment 1 | 69.4 | 0.154 | 10.32 | 86.8 |

The liquid crystal compounds of Comparative Example 1, Comparative Example 2, and Embodiment 1 are liquid crystal compounds represented by the following Formulae 6 to 8, respectively. The liquid crystal compound of Chemical Formula 8 is substantially the same liquid crystal compound as Formula 1-1-1.

Formula 6

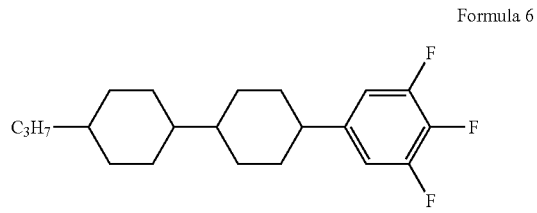

Formula 7

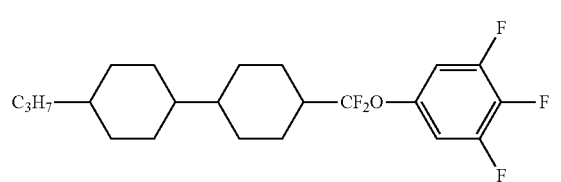

Formula 8

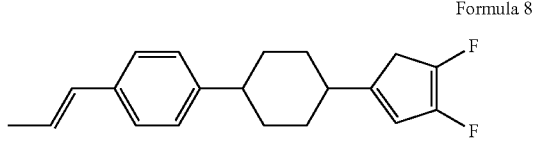

Dielectric anisotropies of Comparative Example 1 and Comparative Example 2 may be about 9.7 and about 9.8, respectively. A dielectric anisotropy of Embodiment 1 may be about 10.32. Thus, the dielectric anisotropies of Comparative Example 1, Comparative Example 2, and Embodiment 1 may be substantially equal to each other.

Refractive anisotropies and nematic phase-isotropic phase transition temperatures of Comparative Example 1, Comparative Example 2, and Embodiment 1 may be substantially equal to each other.

Rotational viscosities of Comparative Example 1 and Comparative Example 2 may be about 160 mPa·s and about 184 mPa·s, respectively. A rotational viscosity of Embodiment 1 may be about 86.8 mPa·s. Accordingly, the liquid crystal compound of Embodiment 1 may have a relatively low rotational viscosity as compared with Comparative Example 1 and Comparative Example 2.

2. Exemplary Properties of Liquid Crystal Compounds

Exemplary property values of liquid crystal compounds of Comparative Example 3, Comparative Example 4, and Embodiment 2 are shown in Table 2.

TABLE 2

| Liquid Crystal Compound | Tni (° C.) | Δn | Δε | γ1 (mPa · s) |
|---|---|---|---|---|
| Comparative Example 3 | 91 | 0.14 | 14.73 | 158 |
| Comparative Example 4 | 195 | 0.152 | 15.0 | 290 |
| Embodiment 2 | 53.8 | 0.216 | 15.29 | 65 |

The liquid crystal compounds of Comparative Example 3, Comparative Example 4, and Embodiment 2 are liquid crystal compounds represented by the following Formulae 9 to 11, respectively. The liquid crystal compound of Formula 11 is substantially the same liquid crystal compound as Formula 1-1-2.

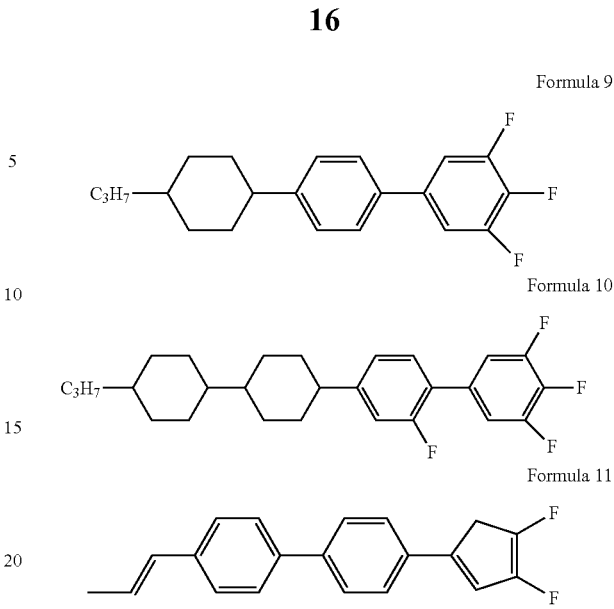

Formula 9

Formula 10

Formula 11

Dielectric anisotropies of Comparative Example 3 and Comparative Example 3 may be about 14.73 and about 15.0, respectively. A dielectric anisotropy of Embodiment 2 may be about 15.29. Thus, the dielectric anisotropies of Comparative Example 3, Comparative Example 4, and Embodiment 2 may be substantially equal to each other.

Refractive anisotropies and nematic phase-isotropic phase transition temperatures of Comparative Example 3, Comparative Example 4, and Embodiment 2 may be substantially equal to each other.

Rotational viscosities of Comparative Example 3 and Comparative Example 4 may be about 158 mPa·s and about 290 mPa·s, respectively. A rotational viscosity of Embodiment 2 may be about 65 mPa·s. Accordingly, the liquid crystal compound of Embodiment 2 may have a relatively low rotational viscosity as compared with Comparative Example 3 and Comparative Example 3.

3. Exemplary Properties of Liquid Crystal Compositions (1) Comparative Example 5

A liquid crystal composition of Comparative Example 5 may be prepared by mixing liquid crystal compounds in the following contents, and property values of the liquid crystal composition may be obtained. The exemplary property values of the liquid crystal compounds are shown in Table 3.

TABLE 3

| Liquid Crystal Compounds | Content (% by weight) |
|---|---|
| 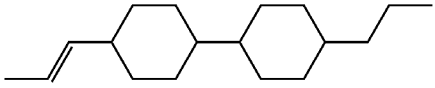 | 21 |
| 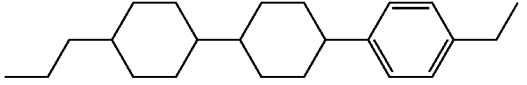 [SMILES: CCCC1CCC(C2CCC(c3ccc(CC)cc3)CC2)CC1] | 10 |

TABLE 3-continued

| Liquid Crystal Compounds | Content (% by weight) |
|---|---|
| 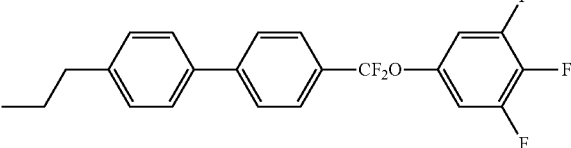 | 17 |
| 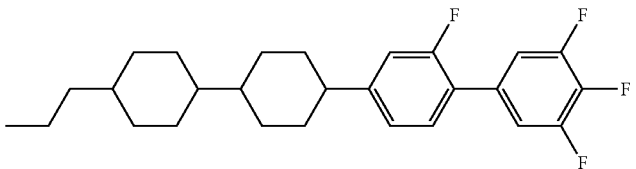 [SMILES: CCCC1CCC(C2CCC(c3ccc(-c4cc(F)c(F)c(F)c4)c(F)c3)CC2)CC1] | 5 |
| 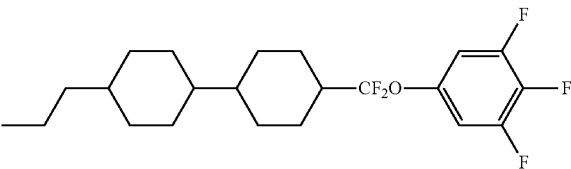 | 20 |
| 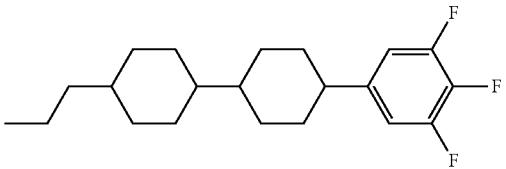 [SMILES: CCCC1CCC(C2CCC(c3cc(F)c(F)c(F)c3)CC2)CC1] | 11 |
| 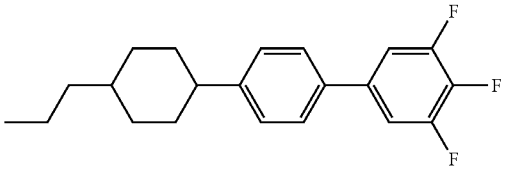 [SMILES: CCCC1CCC(c2ccc(-c3cc(F)c(F)c(F)c3)cc2)CC1] | 16 |
| Tni (° C.) | 0.107 |
| Δn | 9.6 |
| Δε | 119 |
| γ1 (mPa·s) | 88.7 |
| $K_{33}$ | 16.15 |

(2) Embodiment 3

A liquid crystal composition of Embodiment 3 may be prepared by mixing liquid crystal compounds in the following contents, and property values of the liquid crystal composition may be obtained. The exemplary property values of the liquid crystal compounds are shown in Table 4.

TABLE 4

| Liquid Crystal Compounds | Content (% by weight) |
|---|---|
| 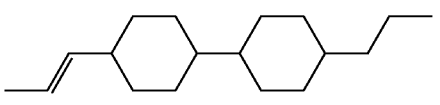 | 21 |
| 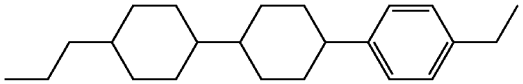 [SMILES: CCCC1CCC(C2CCC(c3ccc(CC)cc3)CC2)CC1] | 10 |

TABLE 4-continued

| Liquid Crystal Compounds | Content (% by weight) |
|---|---|
| 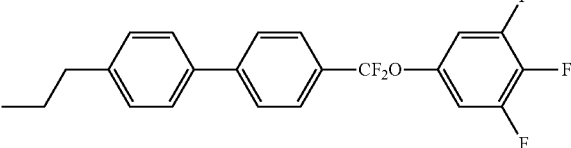 | 17 |
| 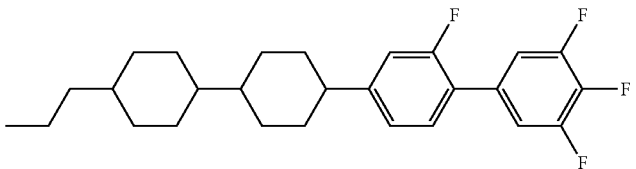 [SMILES: CCCC1CCC(C2CCC(c3ccc(-c4cc(F)c(F)c(F)c4)c(F)c3)CC2)CC1] | 5 |
| 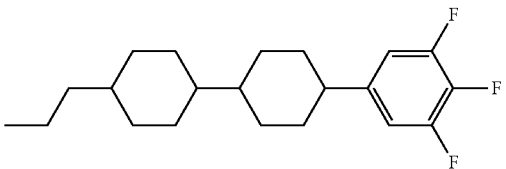 | 6 |
| 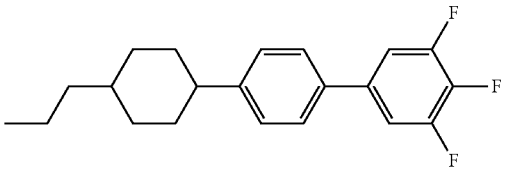 | 16 |
| 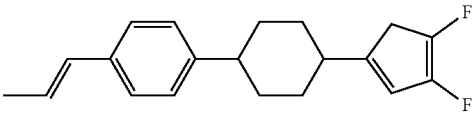 | 25 |
| Tni (° C.) | 0.124 |
| Δ n | 9.3 |
| Δ ε | 112 |
| γ1 (mPa · s) | 84.9 |
| $K_{33}$ | 16.54 |

(3) Embodiment 4

A liquid crystal composition of Embodiment 4 may be prepared by mixing liquid crystal compounds in the following contents, and property values of the liquid crystal composition may be obtained. The exemplary property values of the liquid crystal compounds are shown in Table 5.

TABLE 5

| Liquid Crystal Compounds | Content (% by weight) |
|---|---|
| 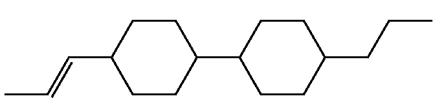 | 21 |
| 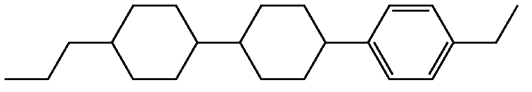 [SMILES: CCCC1CCC(C2CCC(c3ccc(CC)cc3)CC2)CC1] | 10 |

TABLE 5-continued

| Liquid Crystal Compounds | Content (% by weight) |
|---|---|
| 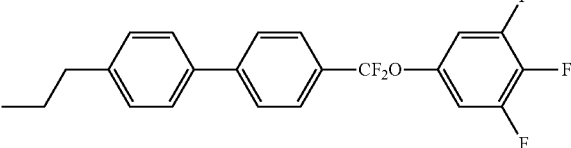 | 17 |
| 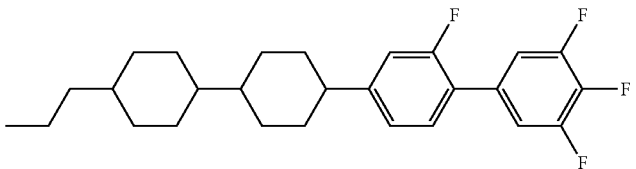 [SMILES: CCCC1CCC(C2CCC(c3ccc(-c4cc(F)c(F)c(F)c4)c(F)c3)CC2)CC1] | 2 |
| 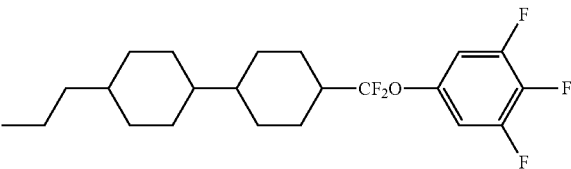 | 20 |
| 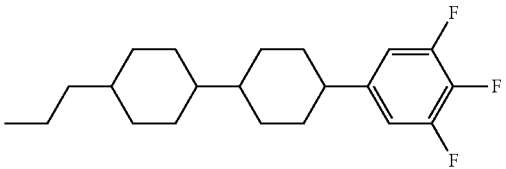 [SMILES: CCCC1CCC(C2CCC(c3cc(F)c(F)c(F)c3)CC2)CC1] | 11 |
| 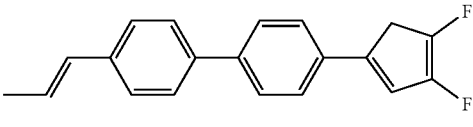 [SMILES: C/C=C/c1ccc(-c2ccc(C3=CC(F)=C(F)C3)cc2)cc1] | 19 |
| Tni (° C.) | 0.122 |
| Δn | 9.8 |
| Δε | 110 |
| γ1 (mPa · s) | 85.3 |
| $K_{33}$ | 16.23 |

(4) Embodiment 5

A liquid crystal composition of Embodiment 5 may be prepared by mixing liquid crystal compounds in the following contents, and property values of the liquid crystal composition may be obtained. The property values of the liquid crystal compounds are shown in Table 6.

TABLE 6

| Liquid Crystal Compounds | Content (% by weight) |
|---|---|
| 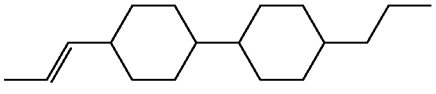 [SMILES: C/C=C/C1CCC(C2CCC(CCC)CC2)CC1] | 21 |
| 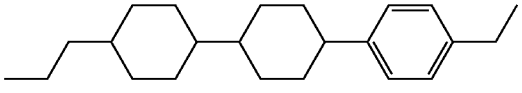 [SMILES: CCCC1CCC(C2CCC(c3ccc(CC)cc3)CC2)CC1] | 10 |

TABLE 6-continued

| Liquid Crystal Compounds | Content (% by weight) |
|---|---|
| [structure: propyl-phenyl-phenyl-CF₂O-trifluorophenyl] | 17 |
| [structure: propyl-cyclohexyl-cyclohexyl-CF₂O-trifluorophenyl] | 3 |
| [structure: propyl-cyclohexyl-cyclohexyl-trifluorophenyl] | 4 |
| [structure: propyl-cyclohexyl-phenyl-trifluorophenyl] | 6 |
| [structure: vinyl-phenyl-cyclohexyl-difluorocyclopentadienyl] | 20 |
| [structure: vinyl-phenyl-phenyl-phenyl-difluorocyclopentadienyl] | 19 |
| Tni (° C.) | 0.136 |
| Δn | 9.8 |
| Δε | 107 |
| γ1 (mPa·s) | 81.7 |
| $K_{33}$ | 16.16 |

The liquid crystal composition of Comparative Example 5 may be a liquid crystal composition including no cyclopentadienyl-based liquid crystal compound. The liquid crystal compositions of Embodiments 3 to 5 may be liquid crystal compositions including 1 or 2 types of cyclopentadienyl-based liquid crystal compounds.

All of the liquid crystal compositions of Comparative Example 5 and Embodiments 3 to 5 may have substantially equal nematic-phase-isotropic phase transition temperatures, dielectric anisotropies, and bending elastic moduli.

The liquid crystal compositions of Comparative Example 5 and Embodiments 3 to 5 may have substantially equal refractive anisotropies. However, refractive anisotropies of Embodiments 3 to 5 are larger as compared a refractive anisotropy of Comparative Example 5. Accordingly, in Embodiments 3 to 5, the liquid crystal display may have a smaller cell gap, as compared with Comparative Example 5. A decrease in cell gap may increase a response speed of the liquid crystal display. Thus, according to an exemplary embodiment of the present invention, the response speed of the liquid crystal display may be increased and cell gap may be decreased.

While a rotational viscosity of Comparative Example 5 may be about 119 mPa·s, rotational viscosities of Embodiments 3 to 5 may be about 112 mPa·s, about 110 mPa·s, and about 107 mPa·s, respectively, which may be smaller values as compared with Comparative Example 5. As compared with Comparative Example 5, Embodiment 3 may have a rotational viscosity of about 94.1%, Embodiment 4 may have a rotational viscosity of about 92.4%, and Embodiment 5 may have a rotational viscosity of about 89.9%. Thus, the rotational viscosities of Embodiments 3 to 5 may be decreased by about 10%, as compared with Comparative Example 5.

4. Exemplary Properties of Liquid Crystal Compositions (1) Comparative Example 6

A liquid crystal composition of Comparative Example 6 may be prepared by mixing liquid crystal compounds in the following contents, and property values of the liquid crystal composition may be obtained. Thus, the exemplary property values of the liquid crystal compounds are shown in Table 7.

TABLE 7

| Liquid Crystal Compounds | Content (% by weight) |
|---|---|
| 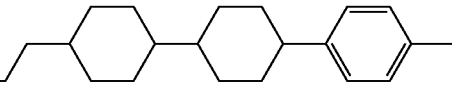 | 30 |
| 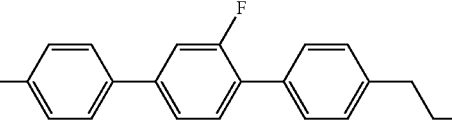 | 2 |
| 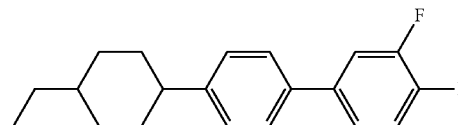 | 10 |
|  | 12 |
|  | 14 |
| 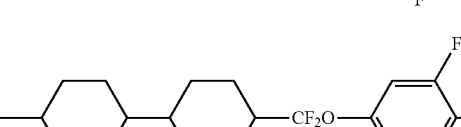 | 11 |
|  | 21 |
| Tni (° C.) | 85.4 |
| Δn | 0.11 |
| Δε | 7.4 |
| γ1 (mPa · s) | 107 |

(2) Embodiment 6

A liquid crystal composition of Embodiment 6 may be prepared by mixing liquid crystal compounds in the following contents, and property values of the liquid crystal composition may be obtained. Thus, the exemplary property values of the liquid crystal compounds are shown in Table 8.

TABLE 8

| Liquid Crystal Compounds | Content (% by weight) |
|---|---|
| 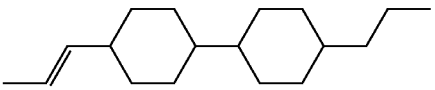 [SMILES: C/C=C/C1CCC(C2CCC(CCC)CC2)CC1] | 32 |
| 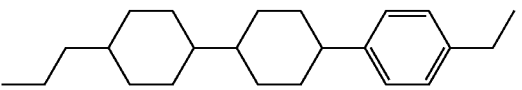 | 2 |
| 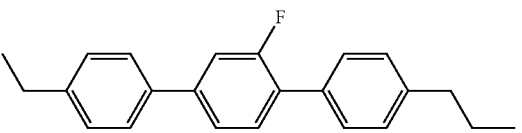 [SMILES: CCCc1ccc(-c2ccc(-c3ccc(CC)cc3)cc2F)cc1] | 10 |
| 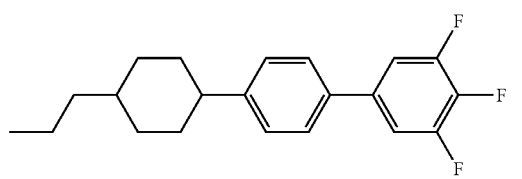 [SMILES: CCCC1CCC(c2ccc(-c3cc(F)c(F)c(F)c3)cc2)CC1] | 12 |
| 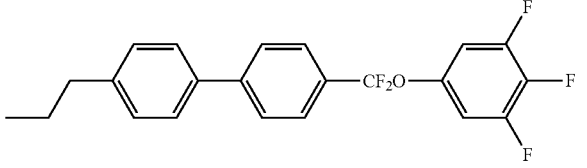 | 14 |
| 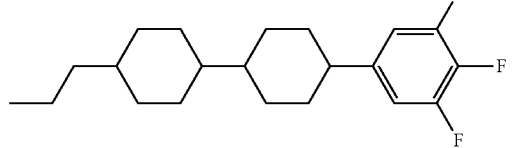 | 5 |
| 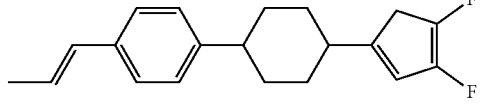 | 25 |
| Tni (° C.) | 82.2 |
| Δn | 0.125 |
| Δε | 7 |
| γ1 (mPa · s) | 102 |

(3) Embodiment 7

A liquid crystal composition of Embodiment 7 may be prepared by mixing liquid crystal compounds in the following contents, and property values of the liquid crystal composition may be obtained. Thus, the exemplary property values of the liquid crystal compounds are shown in Table 9.

TABLE 9

| Liquid Crystal Compounds | Content (% by weight) |
| --- | --- |
| 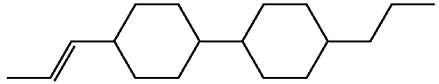 [SMILES: C/C=C/C1CCC(C2CCC(CCC)CC2)CC1] | 32 |
| 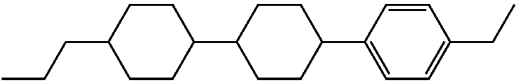 | 2 |
| 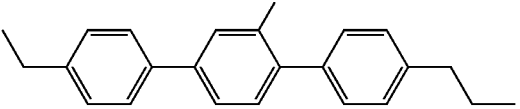 | 10 |
| 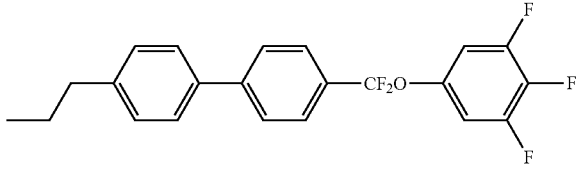 | 14 |
| 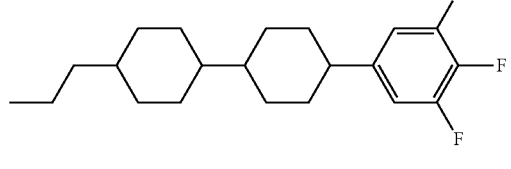 | 11 |
| 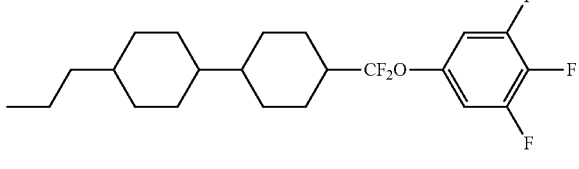 | 21 |
| 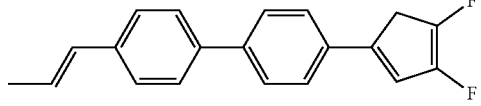 | 10 |
| Tni (° C.) | 85.2 |
| Δn | 0.117 |
| Δε | 7.2 |
| γ1 (mPa · s) | 103 |

(4) Embodiment 8

A liquid crystal composition of Embodiment 8 may be prepared by mixing liquid crystal compounds in the following contents, and property values of the liquid crystal composition may be obtained. Thus, the exemplary property values of liquid crystal compounds are shown in Table 10.

TABLE 10

| Liquid Crystal Compounds | Content (% by weight) |
|---|---|
| 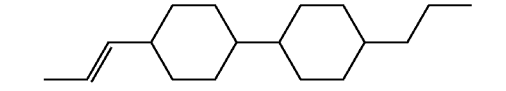 | 35 |
| 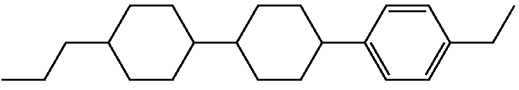 | 2 |
| 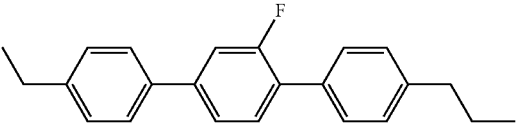 | 10 |
| 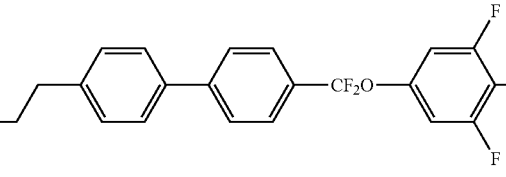 | 14 |
| 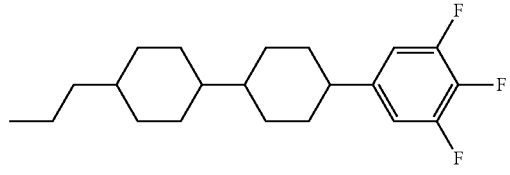 [SMILES: CCCC1CCC(C2CCC(c3cc(F)c(F)c(F)c3)CC2)CC1] | 4 |
| 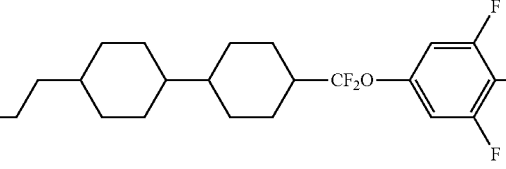 | 3 |
| 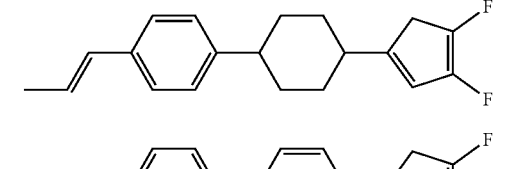 | 20 |
| 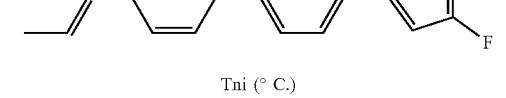 | 12 |
| Tni (° C.) | 82.2 |
| Δ n | 0.129 |
| Δ ε | 6.9 |
| γ1 (mPa · s) | 98 |

The liquid crystal composition of Comparative Example 6 may be a liquid crystal composition including no cyclopentadienyl-based liquid crystal compound. The liquid crystal compositions of Embodiments 6 to 8 may be liquid crystal compositions including 1 or 2 types of cyclopentadienyl-based liquid crystal compounds.

All of the liquid crystal compositions of Comparative Example 6 and Embodiments 6 to 8 may have substantially equal nematic-phase-isotropic phase transition temperatures, dielectric anisotropies, and bending elastic moduli.

The liquid crystal compositions of Comparative Example 6 and Embodiments 6 to 8 may have substantially equal refractive anisotropies. However, as compared with Comparative Example 6 having a refractive anisotropy of about 0.11, the refractive anisotropies of Embodiments 6 to 8 may be about 0.125, about 0.117, and about 0.129, respectively. Accordingly, in Embodiments 6 to 8, the liquid crystal display may have a smaller cell gap, as compared with Comparative Example 6. A decrease in cell gap may increase a response speed of the liquid crystal display. Thus, according to exemplary embodiments of the present invention, the response speed of the liquid crystal display may be increased and cell gap may be decreased.

While a rotational viscosity of Comparative Example 6 may be about 107 mPa·s, rotational viscosities of Embodiments 6 to 8 may be about 102 mPa·s, about 103 mPa·s, and about 98 mPa·s, respectively.

According to exemplary embodiments of the present invention, a liquid crystal composition having a relatively low viscosity and a liquid crystal display including the same may be provided.

It should be understood that exemplary embodiments of the present invention described herein should be considered in a descriptive sense only and not for purposes of limitation. Descriptions of features or aspects within each exemplary embodiment should be considered as available for other similar features or aspects in other exemplary embodiments.

While one or more exemplary embodiments of the present invention have been described with reference to the figures, it will be understood by those of ordinary skill in the art that various changes in form and details may be made therein without departing from the spirit and scope of the present invention.

What is claimed is:

1. A liquid crystal display, comprising:

a first base substrate;

a second base substrate disposed opposite to the first base substrate;

an electrode part disposed on at least one of the first base substrate and the second base substrate; and a liquid crystal layer disposed between the first base substrate and the second base substrate, the liquid crystal layer including a liquid crystal composition, wherein the liquid crystal composition comprises at least one liquid crystal compound represented by Formulae 1 to 3:

Formula 1

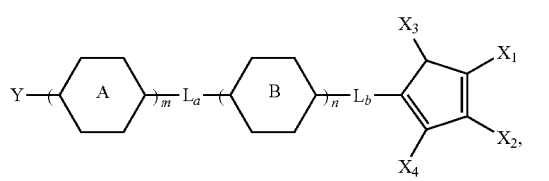

Formula 2

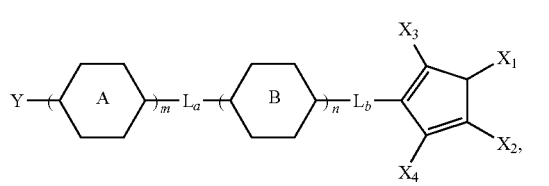

Formula 3

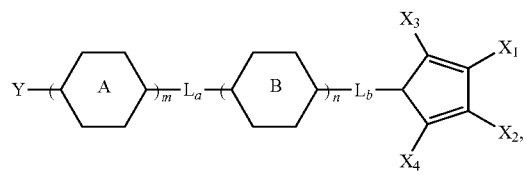

wherein Y is selected from –H or an alkyl group of 1 to 10 carbon atoms, wherein one or more —$CH_2$— groups are each independently unsubstituted or substituted by —C≡C—, —CH=CH—, —$CF_2$O—, —O—, —CO—O—, —O—CO—, or —O—CO—O— such that O atoms are not linked directly to each other, and a hydrogen atom is unsubstituted or substituted by a halogen atom, A and B are each independently selected from 1,4-cyclohexylene or 1,4-phenylene, and —H of A and B are each independently unsubstituted or substituted by —F, —Cl, —$OCF_3$, —$CF_3$, —$CHF_2$, —$CH_2F$, or an alkyl or an alkoxy group of 1 or 2 carbon atoms, n and m are each independently an integer selected from 0 to 2, $X_1$ to $X_4$ are each independently selected from —H, —F, or —Cl, or an alkyl group of 1 or 2 carbon atoms, and $L_a$ and $L_b$ are each independently selected from a single bond, —C≡C—, —COO—, —OCO—, —$CF_2$O—, —$OCF_2$—, —$CH_2$O—, —CO—, —O—, —$(CH_2)_2$—, or —CH=CH—.

2. The liquid crystal display of claim 1, wherein the liquid crystal compounds of Formulae 1 to 3 are in an amount of more than 0% by weight to less than or equal to about 40% by weight with respect to the total liquid crystal composition.

3. The liquid crystal display of claim 1, wherein the liquid crystal compound of Formula 1 includes at least one liquid crystal compound represented by Formula 1-1:

Formula 1-1

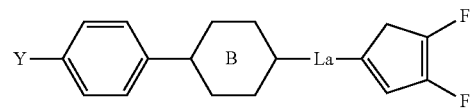

wherein B, $L_a$, and Y are the same as defined in Formula 1.

4. The liquid crystal display of claim 3, wherein the liquid crystal compound of Formula 1-1 includes at least one liquid crystal compound represented by Formulae 1-1-1 and 1-1-2:

Formula 1-1-1

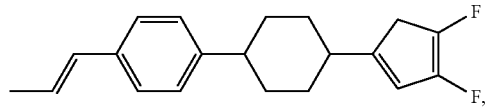

Formula 1-1-2

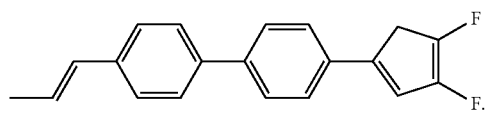

5. The liquid crystal display of claim 1, wherein the liquid crystal composition further includes at least one liquid crystal compound represented by Formula 4:

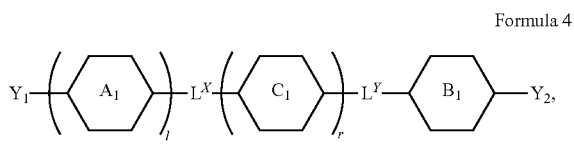

Formula 4 wherein $Y_1$ and $Y_2$ are each independently selected from —F, —Cl, or an alkyl group of 1 to 15 carbon atoms, wherein one or more —$CH_2$— groups are each independently unsubstituted or substituted by —C≡C—, —CH=CH—, —$CF_2$O—, —O—, —CO—O—, —O—CO—, or —O—CO—O— such that O atoms are not linked directly to each other, and a hydrogen atom is unsubstituted or substituted by a halogen atom, $A_1$, $B_1$, and $C_1$ are each independently selected from 1,4-cyclohexylene or 1,4-phenylene, and —H of $A_1$, $B_1$, and $C_1$ are each independently unsubstituted or substituted by —F, —Cl, —$OCF_3$, —$CF_3$, —$CF_2$, —$CH_2F$, or an alkyl or an alkoxy group of 1 or 2 carbon atoms, l and r are each independently an integer selected from 0 to 2, and $L^X$ and $L^Y$ are each independently selected from a single bond, —C≡C—, —COO—, —OCO—, —$CF_2$O—, —$OCF_2$—, —$CH_2$O—, —CO—, —O—, —$(CH_2)_2$—, or —CH=CH—.

6. The liquid crystal display of claim 1, wherein the liquid crystal composition has a positive dielectric anisotropy.

7. The liquid crystal display of claim 1, wherein the liquid crystal layer is driven in a twisted nematic (TN) mode, an in-plane switching (IPS) mode, a plane-to-line switching (PLS) mode, or a fringe field switching (FFS) mode.

8. The liquid crystal display of claim 1, wherein the liquid crystal compounds of Formulae 1 and 2 are in an amount of more than 0% by weight to less than or equal to about 40% by weight with respect to the total liquid crystal composition.

9. A liquid crystal composition, comprising: at least one liquid crystal compound represented by Formulae 1 to 3:

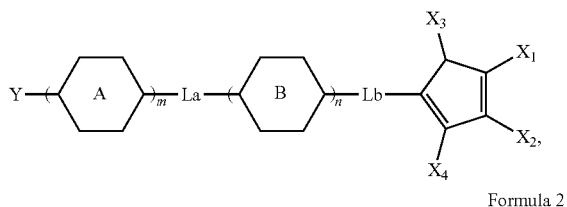

Formula 1

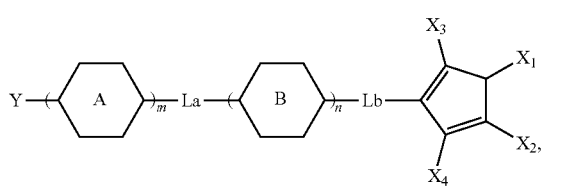

Formula 2

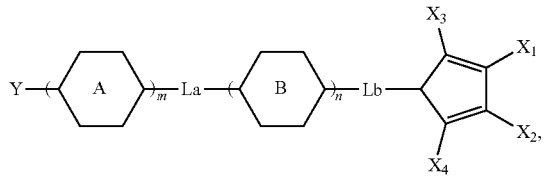

Formula 3 wherein Y is selected from —H or an alkyl group of 1 to 10 carbon atoms, wherein one or more —$CH_2$— groups are each independently unsubstituted or substituted by —CH=CH—, —$CF_2$O—, —O—, —CO—O—, —O—CO—, or —O—CO—O— such that O atoms are not linked directly to each other, and a hydrogen atom is unsubstituted or substituted by a halogen atom, A and B are each independently selected from 1,4-cyclohexylene or 1,4-phenylene, and —H of A and B are each independently unsubstituted or substituted by —F, —Cl, —$OCF_3$, —$CF_3$, —$CHF_2$, —$CH_2F$, or an alkyl or an alkoxy group of 1 or 2 carbon atoms, n and m are each independently an integer selected from 0 to 2, $X_1$ to $X_4$ are each independently selected from —H, —F, or —Cl, or an alkyl group of 1 or 2 carbon atoms, and $L_a$ and $L_b$ are each independently selected from a single bond, —C≡C—, —COO—, —OCO—, —$CF_2$O—, —$OCF_2$—, —$CH_2$O—, —CO—, —O—, —$(CH_2)_2$—, or —CH=CH—.

10. The liquid crystal composition of claim 9, wherein the liquid crystal compounds of Formulae 1 to 3 are in an amount of more than about 0% by weight to less than or equal to about 40% by weight with respect to the total liquid crystal composition.

11. The liquid crystal composition of claim 9, wherein the liquid crystal compound of Formula 1 includes at least one liquid crystal compound represented by Formula 1-1:

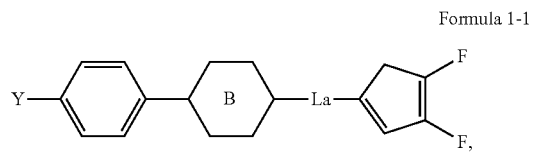

Formula 1-1 wherein B, $L_a$, and Y are the same as defined in Formula 1.

12. The liquid crystal composition of claim 11, wherein the liquid crystal compound of Formula 1-1 includes at least one liquid crystal compound represented by Formulae 1-1-1 and 1-1-2:

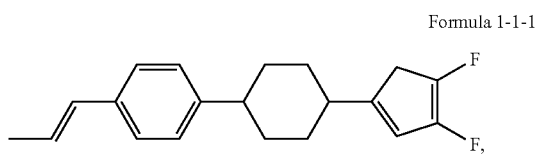

Formula 1-1-1

-continued

Formula 1-1-2

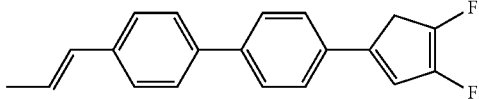

13. The liquid crystal composition of claim 9, wherein the liquid crystal composition further includes at least one crystal compound represented by Formula 4:

Formula 4

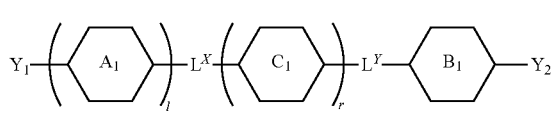

wherein $Y_1$ and $Y_2$ are each independently selected from —F, —Cl, or an alkyl group of 1 to 15 carbon atoms, wherein one or more —CH$_2$— groups are each independently unsubstituted or substituted by —C≡C—, —CH═CH—, —CF$_2$O—, —O—, —CO—O—, —O—CO—, or —O—CO—O— such that O atoms are not linked directly to each other, and a hydrogen atom is unsubstituted or substituted by a halogen atom, $A_1$, $B_1$, and $C_1$ are each independently selected from 1,4-cyclohexylene or 1,4-phenylene, and —H of $A_1$, $B_1$, and $C_1$ are each independently unsubstituted or substituted by —F, —Cl, —OCF$_3$, —CF$_3$, —CHF$_2$, —CH$_2$F, or an alkyl or an alkoxy group of 1 or 2 carbon atoms, l and r are each independently an integer selected from 0 to 2, and $L^X$ and $L^Y$ are each independently selected from a single bond, —C≡C—, —COO—, —OCO—, —CF$_2$O—, —OCF$_2$—, —C$_2$O—, —CO—, —O—, —(CH$_2$)$_2$—, or —CH═CH—.

14. The liquid crystal composition of claim 9, wherein the liquid crystal composition has a positive dielectric anisotropy.

15. The liquid crystal composition of claim 9, wherein the liquid crystal composition is included in a liquid crystal layer, and the liquid crystal layer is driven in a twisted nematic (TN) mode, an in-plane switching (IPS) mode, a plane-to-line switching (PLS) mode, or a fringe field switching (FFS) mode.

16. The liquid crystal composition of claim 9, Wherein the liquid crystal compounds of Formulae 1 and 2 are in an amount of more than 0% by weight to less than or equal to about 40% by weight with respect to the total liquid crystal composition.

17. A liquid crystal display, comprising:
a first base substrate;
a second base substrate disposed opposite to the first base substrate; and
a liquid crystal layer disposed between the first base substrate and the second base substrate, the liquid crystal layer including a liquid crystal composition,
wherein the liquid crystal composition comprises at least one liquid crystal compound represented by Formulae 1 to 3, and the liquid crystal compounds of Formulae 1 to 3 are in an amount of more than 0% by weight to less than or equal to about 40% by weight with respect to the total liquid crystal composition:

Formula 1

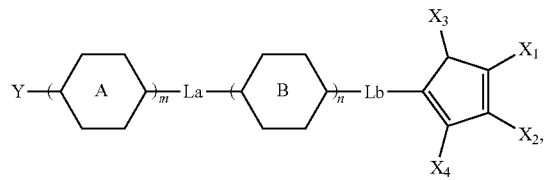

Formula 2

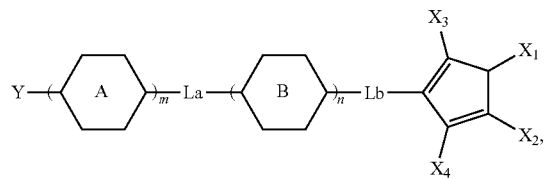

Formula 3

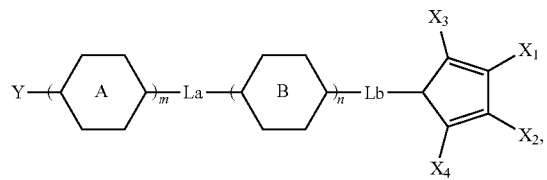

wherein Y is selected from —H or an alkyl group of 1 to 10 carbon atoms, wherein one or more —CH$_2$— groups are each independently unsubstituted or substituted by —C≡C—, —CH═CH—, —CF$_2$O—, —O—, —CO—O—, —O—CO—, or —O—CO—O— such that O atoms are not linked directly to each other, and a hydrogen atom is unsubstituted or substituted by a halogen atom, A and B are each independently selected from 1,4-cyclohexylene or 1,4-phenylene, and —H of A and B are each independently unsubstituted or substituted by —F, —Cl, —OCF$_3$, —CF$_3$, —CHF$_2$, —CH$_2$F, or an alkyl or an alkoxy group of 1 or 2 carbon atoms, n and m are each independently an integer selected from 0 to 2, $X_1$ to $X_4$ are each independently selected from —H, —F, or —Cl, or an alkyl group of 1 or 2 carbon atoms, and $L_a$ and $L_b$ are each independently selected from a single bond, —C≡C—, —COO—, —OCO—, —CF$_2$O—, —OCF$_2$—, —CH$_2$O—, —CO—, —O—, —(CH$_2$)$_2$—, or —CH═CH—.

* * * * *